(12) United States Patent
Lin

(10) Patent No.: US 7,343,631 B2
(45) Date of Patent: Mar. 18, 2008

(54) GOGGLES STRUCTURE

(75) Inventor: Titan Lin, Taipei (TW)

(73) Assignee: Gazelle Corporation, Taipei (TW)

( * ) Notice: Subject to any disclaimer, the term of this patent is extended or adjusted under 35 U.S.C. 154(b) by 174 days.

(21) Appl. No.: 11/234,102

(22) Filed: Sep. 26, 2005

(65) Prior Publication Data
US 2007/0033718 A1 Feb. 15, 2007

(30) Foreign Application Priority Data
Aug. 12, 2005 (TW) .............................. 94127581 A

(51) Int. Cl.
*A61F 9/02* (2006.01)
(52) U.S. Cl. ........................................................ 2/448
(58) Field of Classification Search .................... 2/429, 2/441, 443, 448
See application file for complete search history.

(56) References Cited

U.S. PATENT DOCUMENTS

| | | | | |
|---|---|---|---|---|
| 3,945,044 A | * | 3/1976 | McGee et al. ................. | 2/436 |
| 5,617,588 A | * | 4/1997 | Canavan et al. ............... | 2/428 |
| 5,802,622 A | * | 9/1998 | Baharad et al. ................ | 2/434 |
| 6,192,523 B1 | * | 2/2001 | Pan ................................ | 2/428 |
| 6,349,422 B1 | * | 2/2002 | Schleger et al. ............... | 2/431 |
| 2003/0019018 A1 | * | 1/2003 | Markovitz ..................... | 2/441 |
| 2006/0218705 A1 | * | 10/2006 | Chiang .......................... | 2/448 |

* cited by examiner

*Primary Examiner*—Katherine Moran
(74) *Attorney, Agent, or Firm*—Rosenberg, Klein & Lee

(57) ABSTRACT

A goggles structure reduces its overall weight and rigidity to improve the comfort of wearing, which provides better ventilation and prevents its wearing without a lens. The goggles comprise a goggles frame including a frame and a connecting section, a lens, a pair of head strap connecting means, and a head strap. At least one hanging hook is protruded from the top of the frame. A plurality of hanging holes corresponding to the hanging hooks is disposed at the top and bottom of the lens for fixing the lens onto the frame. The head strap latches the head strap connecting means onto both sides of the lens for preventing the lens from falling out accidentally. When the goggles are not used, the latching force disappears and allows its removal for cleaning. A ventilation structure disposed inside the lens is provided to prevent splattering.

15 Claims, 9 Drawing Sheets

GOGGLES STRUCTURE

BACKGROUND OF THE INVENTION

1. Field of the Invention

The present invention relates to a goggles structure that protects a wearer's eyes and prevents foreign matters from entering into the eyes and resists small quantity of splattered liquid or melted metal according to the general safety protection rules.

2. Description of Related Art

Referring to U.S. Pat. No. 5,617,588 entitled "Snap together protective goggle construction with toric lens" and published on Apr. 8, 1997 for the prior art protective goggles, the objectives of the patent include:

1. Fitting different sizes of faces;
2. Avoiding spluttered or sprayed liquid;
3. Producing airflow that can prevent mists formed on the lens; and
4. Providing an adjustable head strap buckle.

However, the aforementioned prior art still has the following shortcomings:

1. The rigid frame disposed between the lens and the face connecting section must have sufficient structural strength to support the face connecting section in order to support the face connecting section of the face contact section, and thus a thicker material is needed. Such frame not only increases the overall weight and causes a burden for wearing, but also increases the overall rigidity so that a better softness cannot be achieved.

2. The performance of the ventilation structure is not good enough, since it has to concurrently take the ventilation and the prevention of liquid spluttering into consideration, particularly when the airflow inside the goggles has several bended positions at the bottom of the internal side and the top of the goggles, and thus the moisture will be attached on the internal side of the lens easily which will affect the wearer's vision.

3. If the transparent lens of the prior art goggles is removed or the head strap is changed, the wearer may forget to reinstall the lens before wearing the goggles. It is not easy for the wearer to find out at the beginning, and there exists a risk of getting injured. Some of the prior art goggles come with a fixed lens, but the fixed lens may come out by accident if there is a strong external force, and it thus exist a potential risk.

In view of the foregoing shortcomings of the prior art, the inventor of the present invention based on years of experience in the related field to conduct extensive researches and experiments, and finally invented a goggles structure in accordance with the present invention to overcoming the foregoing shortcomings.

SUMMARY OF THE INVENTION

Therefore, it is a primary objective of the present invention to provide a goggles structure that reduces the overall weight and rigidity of a pair of goggles, particularly the weight of the frame, so as to provide better softness to improve the comfort of its wearing.

Another objective of the present invention is to provide a goggles structure that gives a better ventilation structure to improve the ventilation effect A further objective of the present invention is to provide a goggles structure that comes with a safety reminder structure. If the wearer forgets to reinstall the lens, the goggles will not be able to wear, and thus can effectively avoid a misuse or damage. In addition, the way of fixing the lens can prevent the lens from falling out from the goggles.

To achieve the foregoing objectives, a goggles structure of the present invention comprises a goggles frame and a lens. The goggles frame includes a rigid frame and an elastic face connecting section coupled to the internal side of the frame. The frame includes an upper wall, a lower wall, and a pair of sidewalls, and the sidewalls are connected to the upper wall and the lower wall, wherein a plurality of hanging hooks is protruded from the upper wall of the frame. The lens includes a front wall, an upper wall extended from the top of the front wall, and a plurality of hanging holes corresponding to the hanging hooks and disposed at the upper wall of the lens for hanging and fixing the lens. The rigid structure of the lens can support the elastic face connecting section and reduce the material of the frame and improve the comfort of wearing.

To achieve the foregoing objectives, a goggles structure of the present invention comprises a goggles frame, a lens, a pair of head strap connecting means, and a head strap. The goggles frame includes a rigid frame, an elastic face connecting section coupled to the internal side of the frame, a plurality of hanging hooks protruded from the upper wall of the frame, and a pair of connecting sections disposed on both sides and protruded forward. The lens includes a front wall, an upper wall extended backward from the top of the front wall, a plurality of hanging holes corresponding to the hanging hooks and disposed on the upper wall of the lens and extended forward from the internal surface of the lens for hanging and fixing the frame onto the lens, a fixing section outwardly protruded from both sides of the lens, and a fixing groove separately defined on each fixing section. An end of each head strap connecting means is connected to the head strap, and the other end passes through both sides of the connecting section of the rigid frame and elastically latches into the fixing groove of the fixing section on both sides of the lens. The pulling force of the head strap connecting means of the head strap is exerted onto the lens in a direction towards the wearer, and thus can prevent the lens from fall out by accident.

To make it easier for our examiner to understand the innovative features and technical content, we use a preferred embodiment together with the attached drawings for the detailed description of the invention, but it should be pointed out that the attached drawings are provided for reference and description but not for limiting the present invention.

DETAILED DESCRIPTION OF PREFERRED EMBODIMENTS

Figure 1:
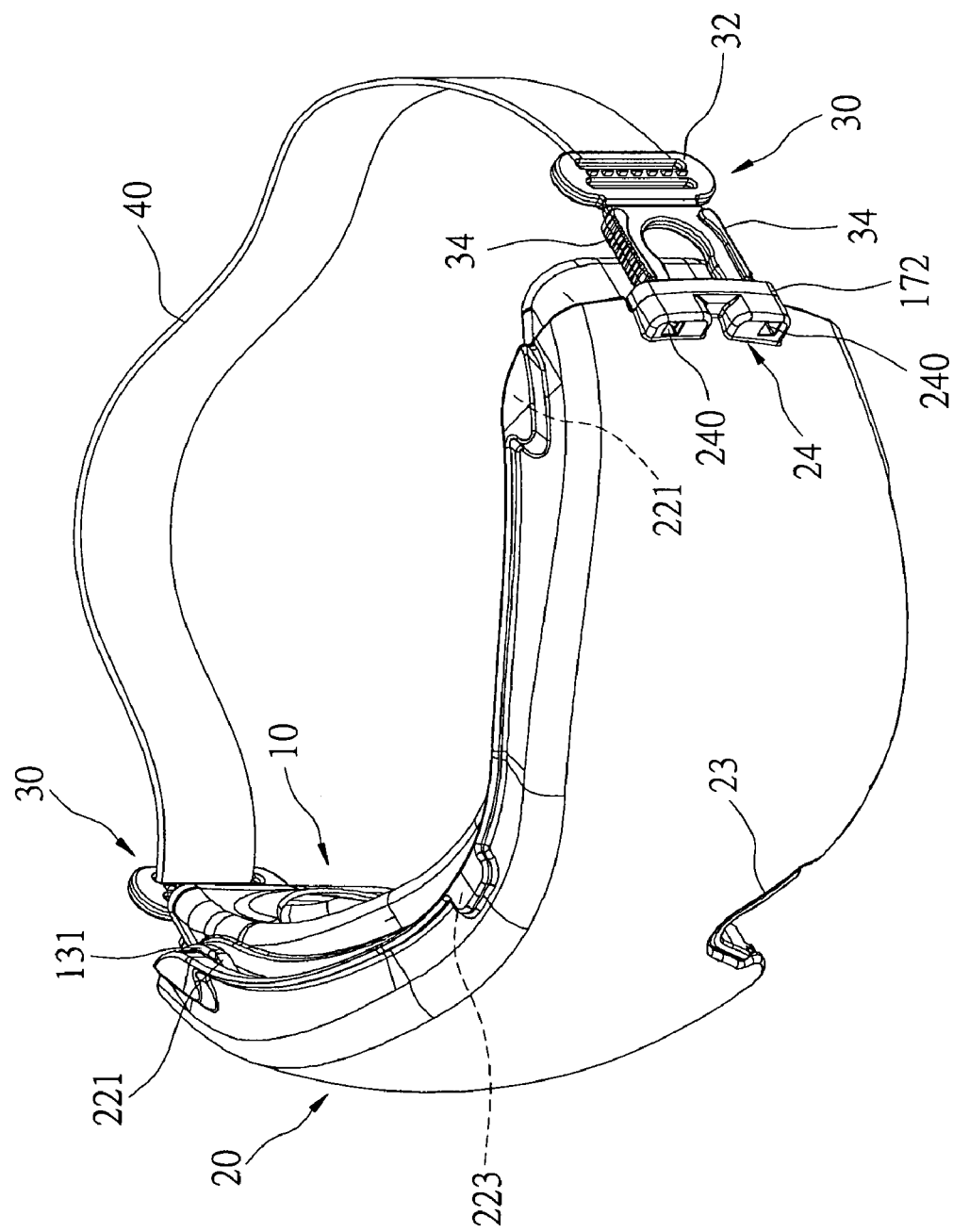
FIG. 1 is a perspective view of a goggles structure of the invention.

Refer to FIG. 1 for the perspective view of a goggles structure of the invention. The present invention provides a goggles structure comprising a goggles frame 10, a lens 20, a pair of head strap connecting means 30, and a head strap 40. The goggles are used for protecting a wearer's eyes, which is applicable for wearing while the wearer is doing exercises, and particularly applicable for preventing objects from hitting the wearer's eyes or liquids from spluttering into the eyes.

Figure 2:
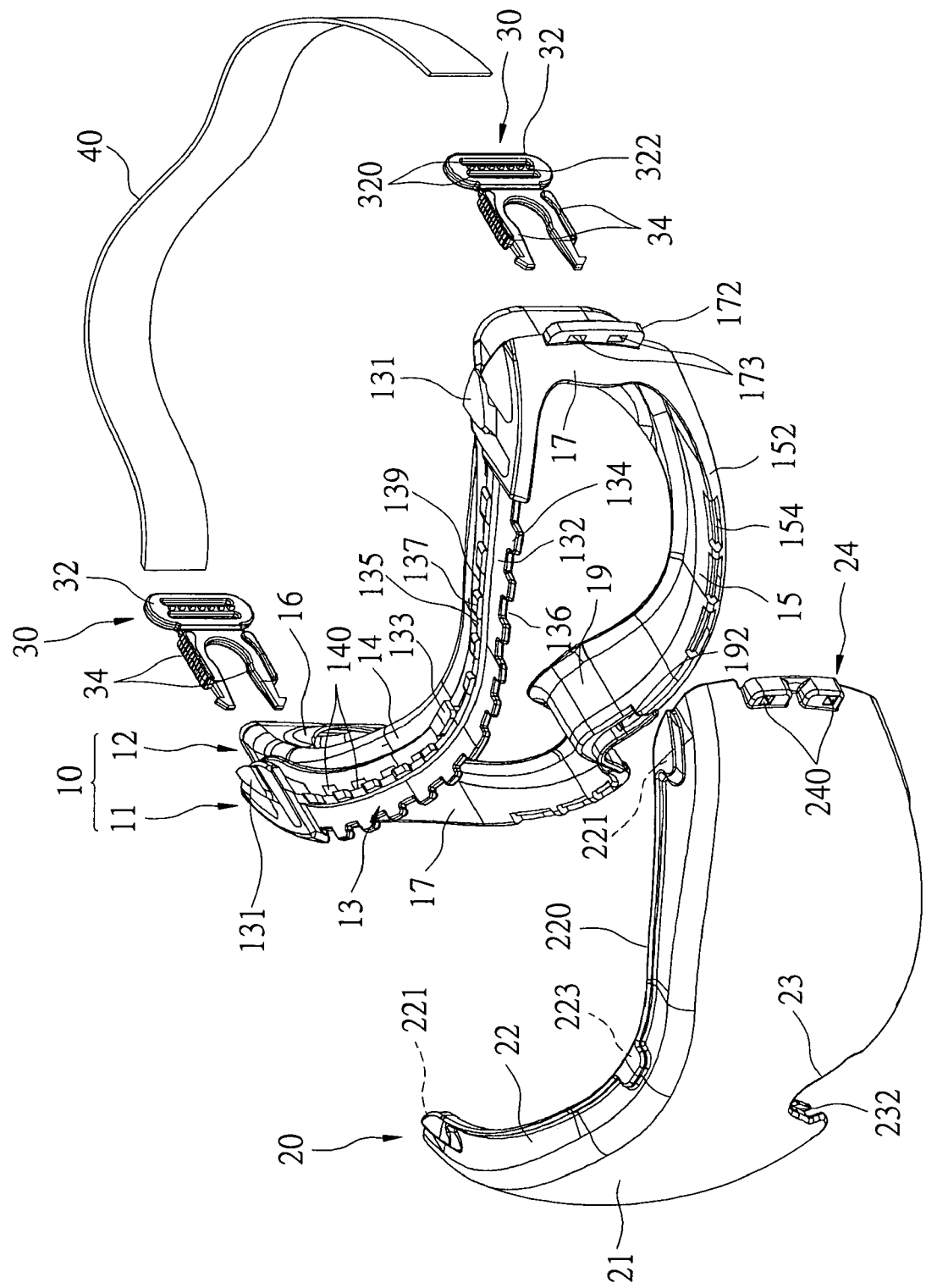
FIG. 2 is an exploded view of a goggles structure of the invention.
Figure 3:
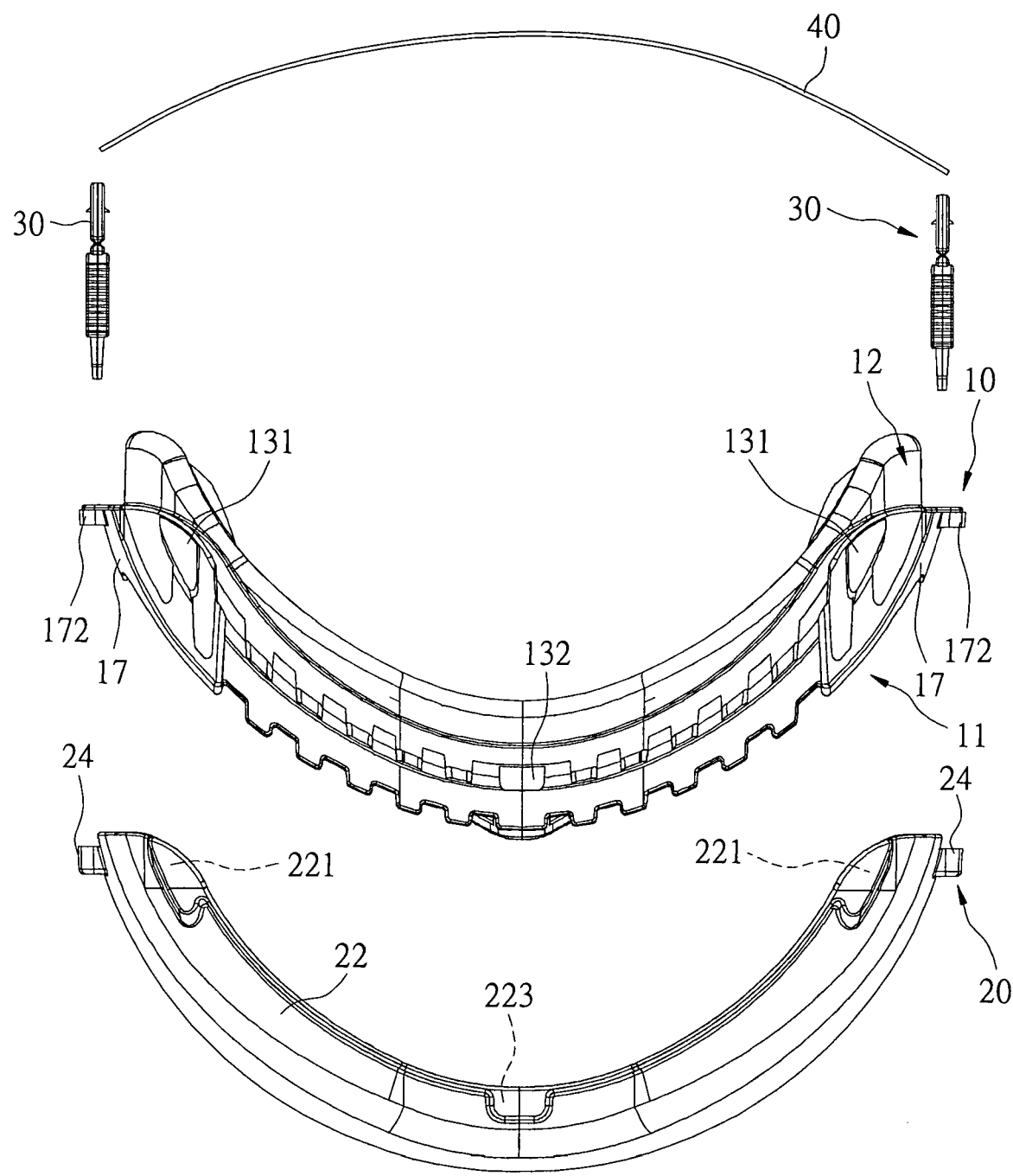
FIG. 3 is a top view of disassembled parts of a goggles structure of the invention.
Figure 4:
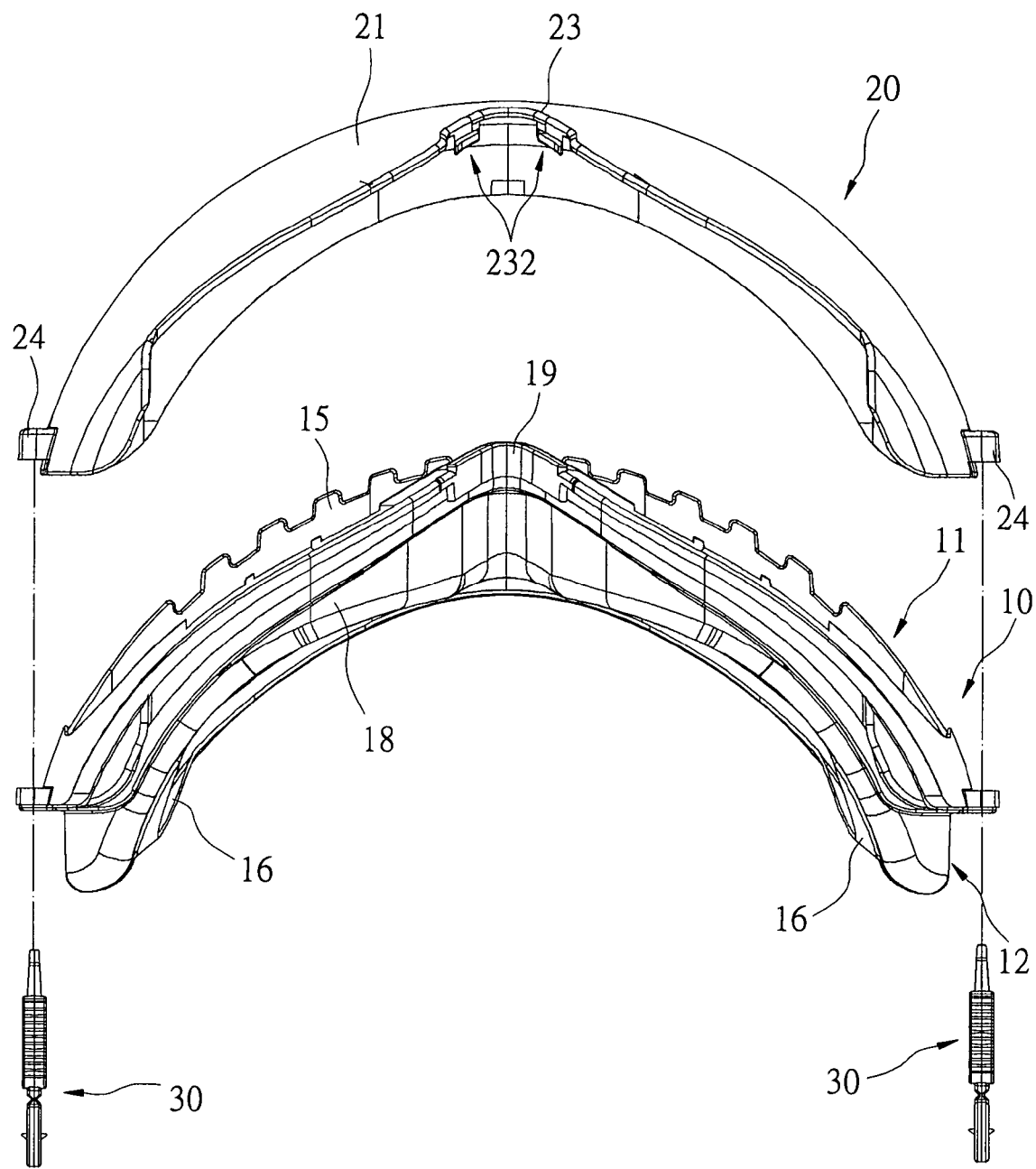
FIG. 4 is a bottom view of disassembled parts of a goggles structure of the invention.

Refer to FIGS. 2 to 4 respectively for the exploded view, top view and bottom view of the of the goggles structure of the present invention. The goggles frame 10 includes a rigid frame 11 and an elastic face connecting section 12. The face connecting section 12 is connected to the internal side of the frame 11, and the face connecting section 12 and the frame 11 are generally coupled with each other by a plastic injection method. The frame 11 can provide appropriate structural strength for the goggles frame 10, so that the face connecting section 12 can be connected softly onto the wearer's face when the wearer wears the goggles.

The frame 11 includes an upper wall 13, a lower wall 15, and a pair of sidewalls 17, wherein at least one hanging hook is protruded upwardly from the upper wall 13. In the present preferred embodiment, three hanging hooks 131, 133 are substantially in inverted T-shape and disposed between the middle and both sides of the frame 11. The sidewalls 17 on both sides of the frame 11 separately include a connecting section 172, and each of the connecting sections 172 forms a pair of penetrating holes 173.

Figure 5:
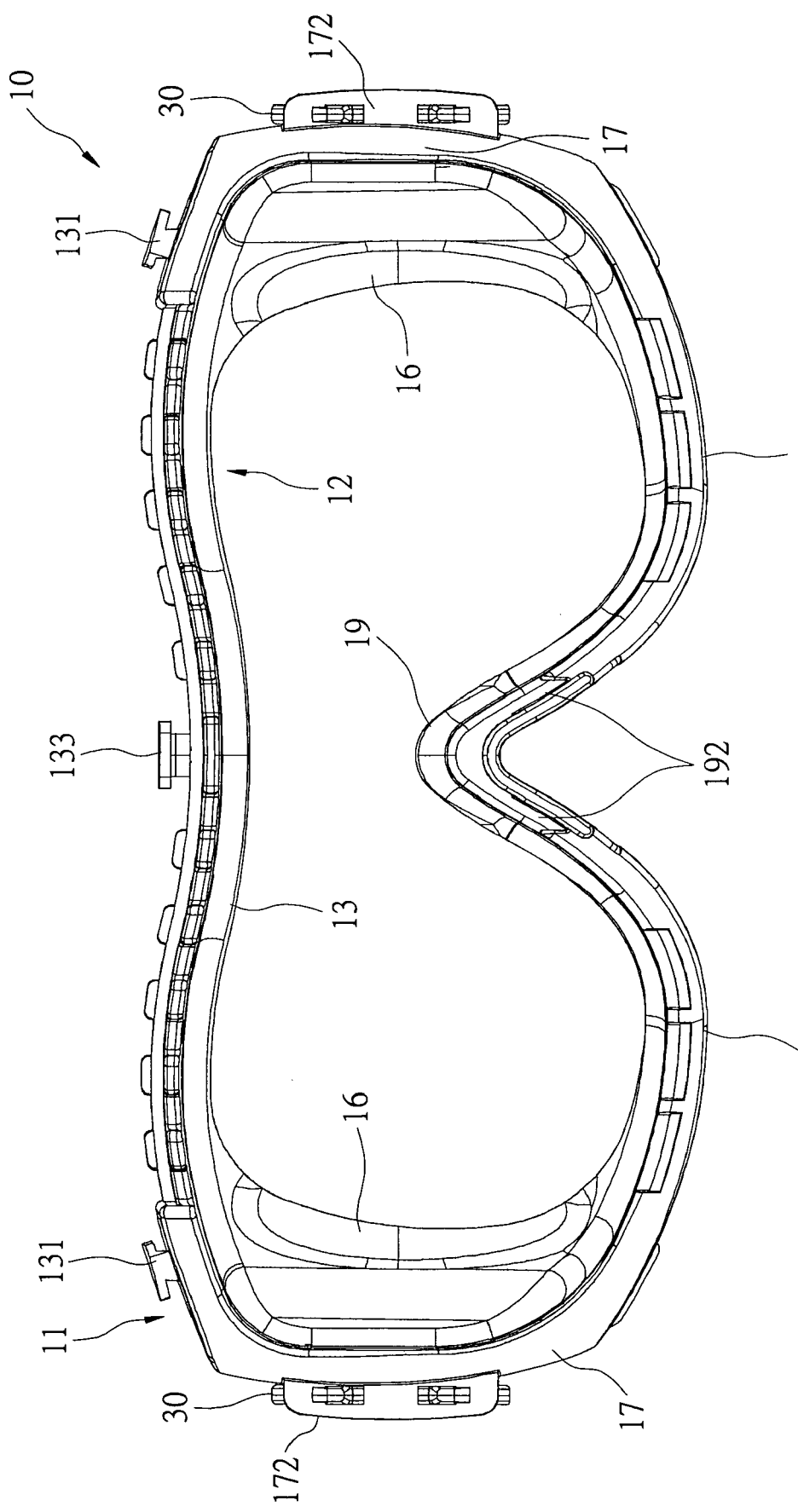
FIG. 5 is a front view of a goggles structure having its lens removed according to the invention.
Figure 7:
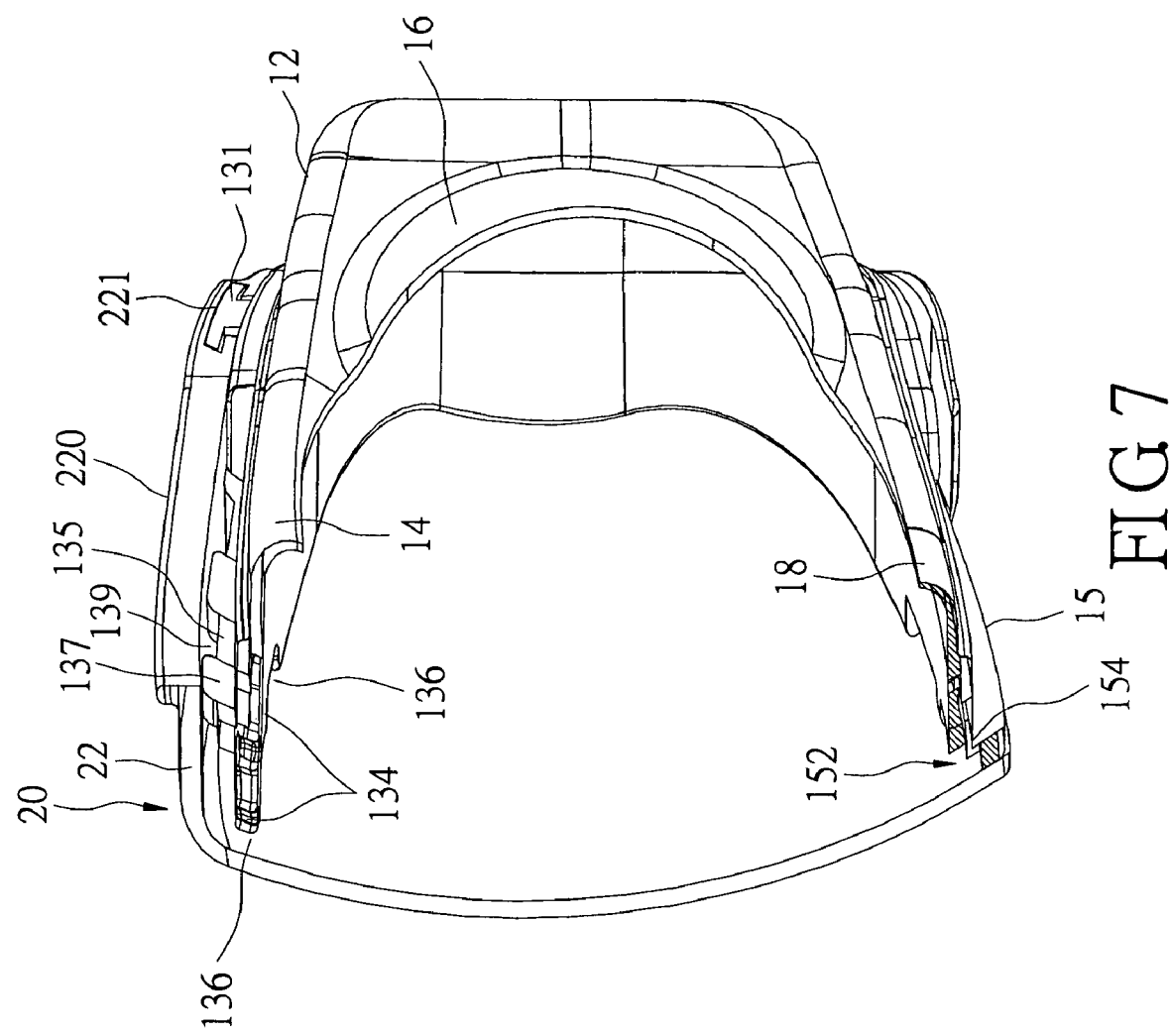
FIG. 7 is a cross-sectional view of a goggles structure of the invention.

Referring to FIG. 5, the face connecting section 12 is made of a soft and flexible material such as a thermal plastic rubber, and includes an upper wall 14, a pair of sidewalls 16, and a lower wall 18 as shown in FIG. 7, so that the face connecting section 12 can be attached softly and tightly onto a wear's face, when the wearer wears the goggles.

Figure 2A:
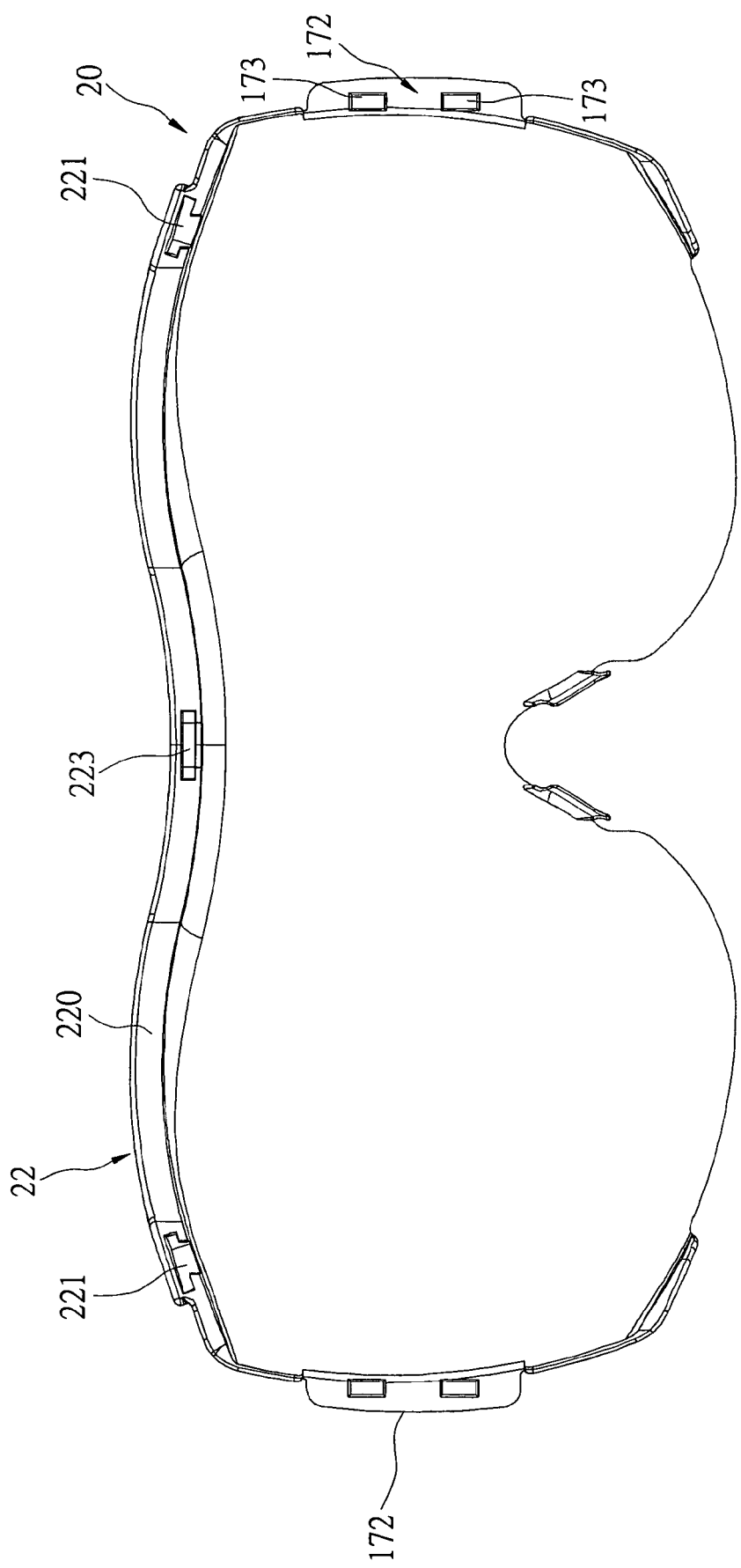
FIG. 2A is a rear side view of a lens of a goggles structure of the invention.

The lens 20 is made of a transparent material and includes a front wall 21 and an upper wall 22 extended backward from the top of the front wall 21. The upper wall 22 of the lens 20 includes a plurality of hanging holes 221, 223 extended inwardly from the internal side of the upper wall 22 as shown in FIG. 2A. and the hanging holes 221, 223 are corresponsive to the hanging hooks 131, 133 for hanging and fixing the frame 11 onto the lens 20. Therefore, the rigid structure of the lens 20 can support the face connecting section 12 to reduce the thickness of the frame 11 and the burden of the wearer. On the other hand, reducing the rigidity can improve the comfort of wearing.

The upper wall 22 of the lens 20 according to the invention comprises a flange 220 extended upward from the upper wall 22 as shown in FIG. 2 for blocking spluttered liquid coming from the front side.

Both sides of the structure of the invention has a characteristic of installing and removing the lens easily, and a fixing section 24 is protruded outward separately from both sides of the lens, and a pair of fixing grooves 240 are formed on the fixing section 24.

Figure 6:
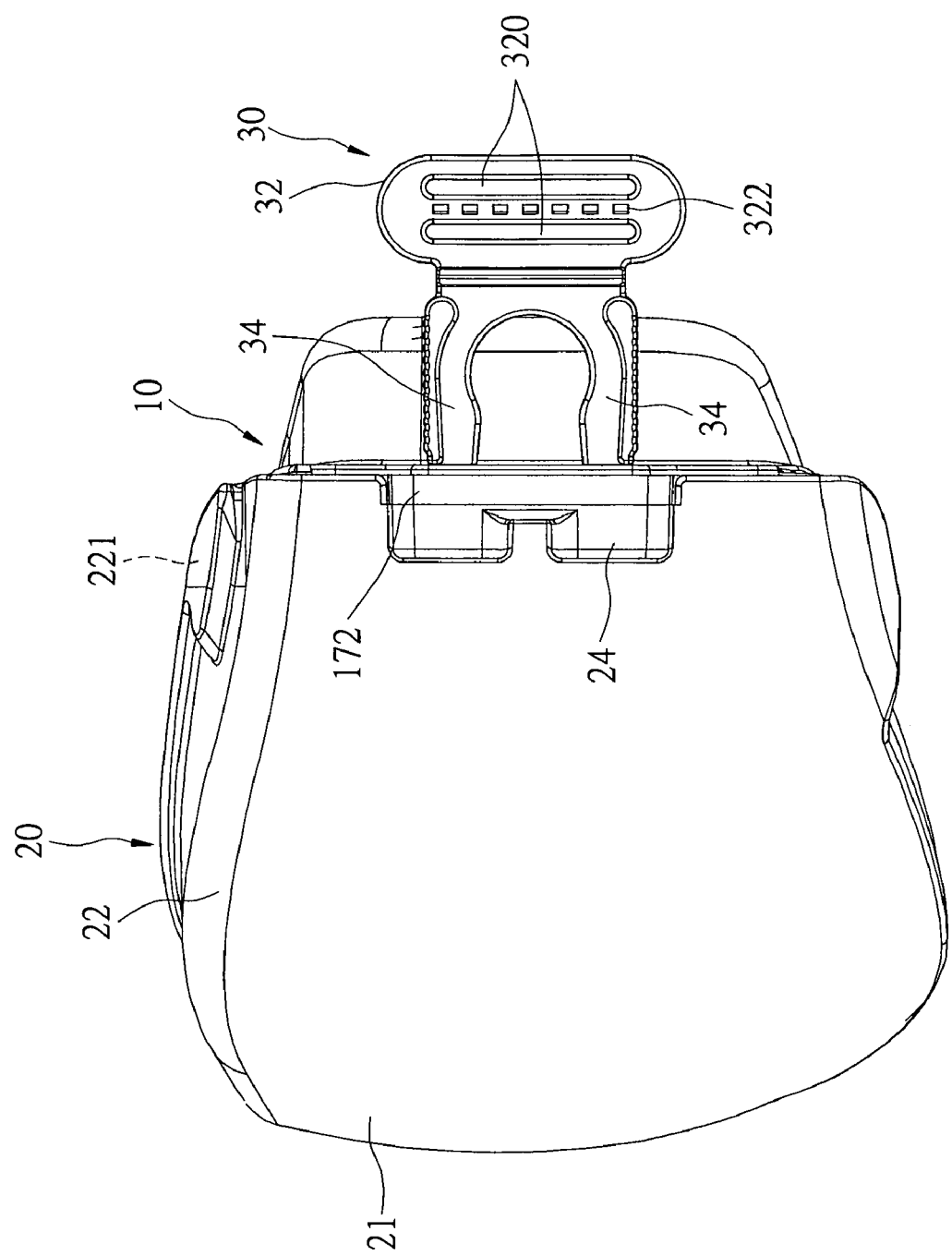
FIG. 6 is a side view of a goggles structure of the invention.
Figure 6A:
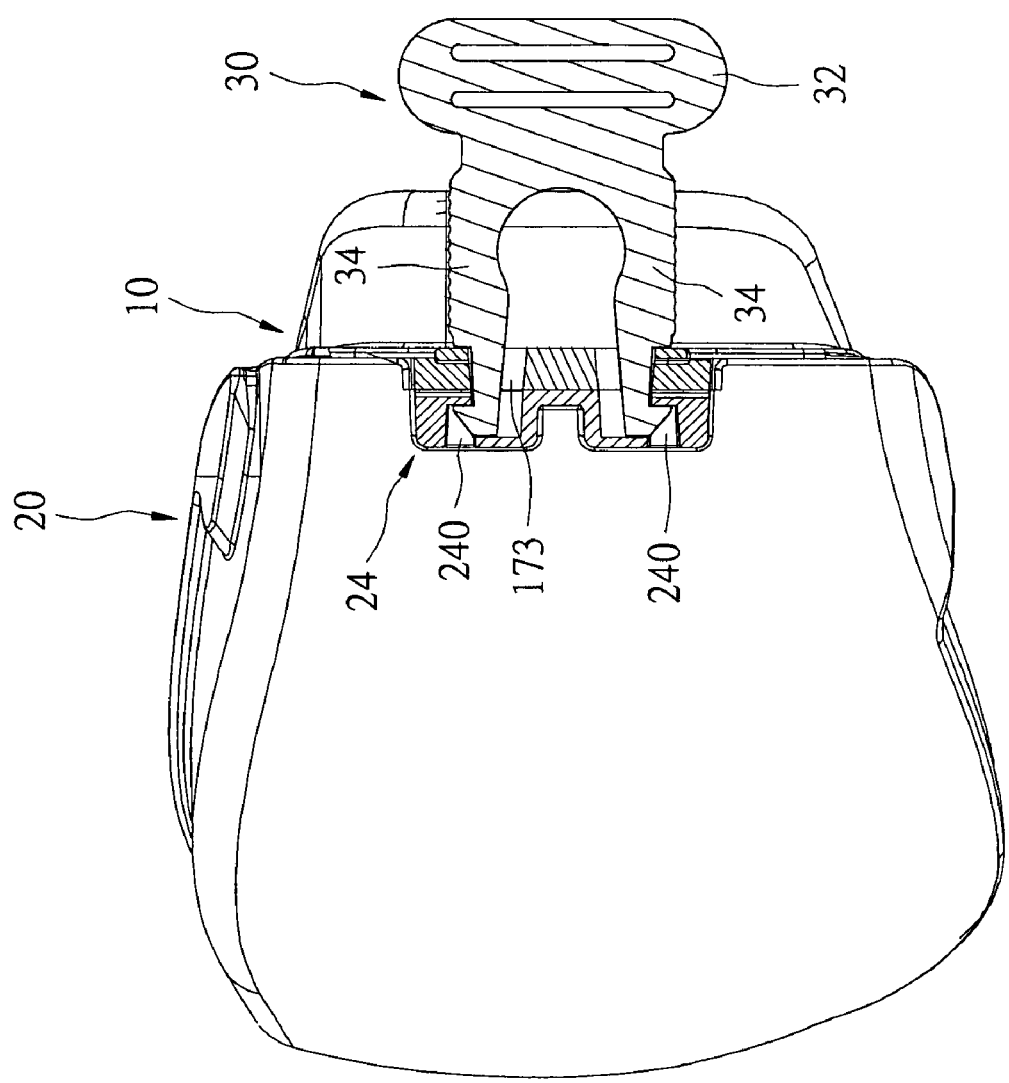
FIG. 6A is a cross-sectional side view along the side of a head strap connecting means of a goggles structure of the invention.

Refer to FIGS. 6 and 6A for the side view and cross-sectional view along the lateral side of the head strap connecting means of goggles structure according to the present invention respectively. The head strap connecting means 30 is substantially U-shaped and includes a connecting section 32 and a pair of hooking sections 34, and the pair of hooking sections 34 is extended forward from the front end of the connecting section 32. The connecting section 32 is provided for connecting the head strap 40 and includes a pair of narrow grooves 320 and a skip-proof pillar 322 disposed between the narrow grooves 320 for passing through and fixing the head strap 40. The pair of hooking sections 34 separately passes through the penetrating holes 173 of the connecting section 172 on both sides of the frame 11, and then passes through the fixing groove 240 of the fixing section 24 on both sides of the lens 20. The pair of hooking sections 34 latches the fixing section 24, and the elastic force of the head strap 40 presses the fixing section 24 tightly against the connecting section 172 of the frame 11.

The invention uses the pulling force produced to press the lens 20 tightly on the goggles frame 10 while wearing the goggles to prevent its falling out. On the other hand, the lens 20 can be installed or removed easily for cleaning, when the goggles are not worn. If the wearer wears the goggles, the head strap connecting means 30 securely attaches lens 20 onto the goggles frame 10 and prevents the lens 20 from falling out by accident by the pulling force produced by the elastic pulling force of the head strap 40 onto the lens 20. In other words, the invention not only secures the lens 20 onto the goggles frame 10, but also prevents the lens 20 from falling out by accident. If the goggles are not in use, the head strap 40 will not produce a pulling force onto the head strap connecting means 30, and thus the head strap connecting means 30 can be removed easily by pressing the pair of hooking sections 34 to separate the connecting section 172. Therefore, the lens 20 can be easily removed for cleaning. If the lens 20 is stained during the wearing, the removal process of the lens very simple and convenient.

Reference is made to FIGS. 2 and 4 for the invention. The middle section of the lens 20 of the goggles structure is latched with the middle section of the frame 11, and thus the lens 20 can be mounted onto the goggles frame 10 more appropriately. More specifically, the middle of the lens 20 forms a sunken mounting section 23, and the mounting section 23 includes at least one inwardly protruded latch plate 232 at its internal side. The rigid frame 11 forms a protruded nose section 19 at the middle of the lower wall 15, and the front end of the nose section 19 forms at least one latch groove 192 corresponding to the latch plate 232. Therefore, the lower edge of the lens 20 is mounted onto the nose section 19 of the frame 11 by the latch plate 232 of the mounting section 23.

The present invention also provides a good ventilation effect to avoid mists in the goggles. Referring to FIG. 2, the upper wall 13 of the frame 11 includes an upwardly protruded protective wall 135 and a forwardly protruded transversal wall 132. The protective wall 135 provides a further protection means to block spluttered liquid from flowing into the goggles. The protective wall 135 and the transversal wall 132 separately include a plurality of protrusions 137, 134 and form a plurality of ventilation grooves 139, 136 between two adjacent protrusions 137, 134. The protrusion 137 of the protective wall 135 is coupled to the bottom of the upper wall of the lens 20, and the protrusion 134 of the transversal wall is coupled onto the internal side of the front wall 21 of the lens 20.

The front end of the lower wall 15 of the frame 11 is bent downward to define a folded edge 152, and the folded edge 152 includes a plurality of rectangular grooves 154 disposed at the top of the folded edge 152, and each groove 154 is interconnected to the bottom of the lower wall 15 of the frame 11, wherein the front wall 21 of the lens 20 is coupled to the folded edge 152.

The upper wall 14 of the face connecting section 12 of the goggles structure of the present invention includes a plurality of containing holes 140 proximate to the protective wall 135, and the protective wall 135 can prevent liquid from flowing into the goggles through the ventilation holes, and the containing hole 140 can contain the liquid and prevent the liquid from spreading further, and thus the liquid will not flow along the top surface of the face connecting section 12. Such arrangement allows users to take off the goggles for cleaning within a short period of time.

Reference is made to FIG. 6A for the cross-sectional view of a goggles structure of the present invention along the lateral side of the head strap connecting means. FIG. 6A shows that the pair of hooking sections 34 of the head strap connecting means 30 latches the lens 20 to the goggles frame 10. The structure of the present invention requires the wearer to remove the goggles to clean the lens 20, and such arrangement can assure the safety of the operation and prevent accidents. When the lens 20 is being removed, the pair of hooking sections 34 is pressed first, and then the lens 20 can be separated from the goggles frame 10 easily for cleaning.

The procedure of installing and removing the lens 20 of the present invention is very simple and easy, so that when the lens is stained, the wearer can clean it immediately. Another characteristic of the invention resides on that if the wearer forgets to reinstall the lens, the head strap connecting means 30 will not be able to latch the goggles frame 10 for the installation, and thus can prevent wearers from wearing the goggles without reinstalling the lens, and thus preventing possible dangers resulted from the misuse.

Reference is made to FIG. 7 for the cross-sectional view of the goggles structure of the present invention. FIG. 7 illustrates a good ventilation structure of the present invention. The groove 154 at the upper wall 15 of the frame 11 allows airflow to flow smoothly and prevents any mist formed within the goggles. If the airflow passes through the internal top section of the lens 20, the plurality of ventilation grooves 136, 139 will be able to reduce the bending of the airflow.

In summation of the description above, the goggles structure of the invention includes the following advantages.

1. The lens is mounted onto the goggles frame by a hanging method. The top and bottom of the frame include a plurality of hanging hooks, and the top and bottom of the lens include a plurality of hanging holes corresponding to the hanging hooks for hanging and mounting the lens onto the frame. The rigid structure of the lens can support the elastic face connecting section, so as to reduce the material and weight of the frame and improve the comfort of wearing.

2. The invention provides a ventilation structure and includes a vertical penetrating holes disposed at the top and bottom of the frame. Such arrangement not only provides better ventilation, but also reduces the material used.

3. In the nose section of the goggles of the invention, the lens uses the discontinuous aslant structure on both sides of the lens and the convex fixing section to cope with the concave latch groove to mount the lens onto the goggles frame.

4. A pair of head strap connecting means is provided, so that when a user wears the head strap, the elastic force produced will fix the frame of the goggles frame and prevent the lens from falling out. Both sides of the head strap connecting means come with a separate hook to latch the lens and the connection section at the external side of the frame.

Unlike the U.S. Pat. No. 5,617,588, the present invention uses the hanging method to mount the lens onto the goggles frame and provides better ventilation. The invention also reinforces the fixing of the leans on the lateral sides, and thus the invention improves over the prior art, and complies with the requirements of the patent application.

Although the present invention has been described with reference to the preferred embodiments thereof, it will be understood that the invention is not limited to the details thereof. Various substitutions and modifications have been suggested in the foregoing description, and others will occur to those of ordinary skill in the art. Therefore, all such substitutions and modifications are intended to be embraced within the scope of the invention as defined in the appended claims.

What is claimed is:

1. A goggles structure, comprising:
a goggles frame, having a rigid frame, and an elastic face connecting section coupled to an internal side of said frame, and said frame having an upper wall, a lower wall, and a pair of sidewalls, and said sidewalls being coupled to said upper wall and said lower wall, wherein said frame includes at least one hanging hook protruded upward from said upper wall, said upper wall of said frame includes an upwardly protruded protective wall and a forwardly protruded transversal wall, and said protective wall and transversal wall separately include a plurality of protrusions and formed a plurality of ventilation grooves disposed between two adjacent protrusions;
a lens, having a front wall and an upper wall extended backward from the top of said front wall, and said upper wall of said lens having a plurality of hanging holes corresponding to said at least one hanging hook for hanging and mounting said frame onto said lens; such that the rigid structure of said lens is capable of supporting an elastic face connecting section to reduce the material of said frame and improve the comfort of wearing.

2. The goggles structure of claim 1, further comprises a pair of head strap connecting means, each having an end coupled to a head strap and the other end passes trough both sides of said rigid frame and latches both sides of said lens, so that when a wearer wears said goggles, said head strap is pressed against said frame by the force produced by said head strap connecting means to prevent said lens from falling out.

3. The goggles structure of claim 2, wherein said frame includes a forwardly protruded connecting section separately disposed on both sides of said frame, and said each connecting section forms a penetrating hole, and said lens includes a fixing section outwardly protruded from both sides of said lens and having a pair of fixing grooves, and said pair of head strap connecting means is substantially U-shaped and includes a connecting section and a pair of hooking sections disposed on both sides of the front end of said connecting section, and said connecting section is coupled to said head strap, and said hooking section passes through said penetrating hole of said connecting section and latches said fixing section.

4. The goggles structure of claim 1, wherein said hanging hook is in an inverted T-shape and said at least one hanging hook is disposed at the middle and on both sides of said frame.

5. The goggles structure of claim 1, wherein said lens forms a sunken mounting section disposed at the middle of said lens, and said mounting section includes at least one inwardly protruded latch plate at the internal side of said mounting section, and said rigid frame forms a protruded nose section disposed at the middle of said lower wall of said rigid frame, and said nose section forms at least one latch groove corresponding to said latch plate and disposed at the front end of said nose section.

6. The goggles structure of claim 1, wherein said protrusion of said protective wall is coupled to the bottom of said upper wall of said lens, and said protrusion of said transversal wall is coupled to the internal side of said front wall of said lens.

7. The goggles structure of claim 1, wherein said lower wall of said frame includes a folded edge bent downward from said lower wall, and the top of said folded edge includes a plurality of rectangular grooves interconnected to the bottom of said lower wall of aid frame, and said front wall of said lens is coupled to said folded edge.

8. The goggles structure of claim 1, wherein a face connecting section comprises a plurality of containing holes disposed at the top of said face connecting section and proximate to said protective wall.

9. A goggles structure, comprising:
a goggles frame, having a rigid frame, and an elastic face connecting section coupled to an internal side of said frame, and said frame having an upper wall with a plurality of upwardly protruded hanging hooks, and both sides of said frame including a pair of forwardly protruded connecting sections;
a lens, having a front wall and an upper wall extended backward from the top of said upper wall, and said upper wall of said lens having a plurality of hanging holes protruded forward from the surface of the internal surface of said upper wall and corresponding to said hanging hooks for hanging and mounting said frame onto said lens, and both sides of said lens separately includes an outwardly protruded fixing section, and said each fixing section forms a pair of fixing grooves;
a head strap, being worn at the head of a wearer; and a pair of head strap connecting means, each having an end coupled to said head strap and the other end passes through said connecting section on both sides of said rigid frame and latches said fixing groove of said fixing section on both sides of said lens, so that the pulling force produced by said head strap and exerted onto the lens in the direction towards said wearer is capable of preventing said lens from falling out.

10. The goggles structure of claim 9, wherein said hanging hook is in an inverted T-shape and said each hanging hook is disposed at the middle and on both sides of said frame.

11. The goggles structure of claim 9, wherein said head strap connecting means is substantially U-shaped and includes a connecting section and a pair of hooking sections disposed on both sides of the front end of said connecting section, and said each connecting section is coupled to said head strap and said hooking section is elastically hooked to said fixing section.

12. The goggles structure of claim 9, wherein said lens forms a sunken mounting section disposed at the middle of said lens, and said mounting section includes at least one inwardly protruded latch plate at the internal side of said mounting section, and said rigid frame forms a protruded nose section disposed at the middle of said lower wall of said rigid frame, and said nose section forms at least one latch groove corresponding to said latch plate and disposed at the front end of said nose section.

13. The goggles structure of claim 9, wherein said upper wall of said frame includes an upwardly protruded protective wall and a forwardly protruded transversal wall, and said protective wall and transversal wall separately include a plurality of protrusions and forms a plurality of ventilation grooves disposed between two adjacent protrusions, and said protrusion of said protective wall is coupled to the bottom of said upper wall of said lens, and said protrusion of said transversal wall is coupled to an internal side of said front wall of said lens.

14. The goggles structure of claim 9, wherein said lower wall of said frame includes a folded edge bent downward from said lower wall, and the top of said folded edge includes a plurality of rectangular grooves interconnected to the bottom of said lower wall of said frame, and said front wall of said lens is coupled to said folded edge.

15. The goggles structure of claim 9, wherein said face connecting section comprises a plurality of containing holes disposed at the top of said face connecting section and proximate to said protective wall.

* * * * *